(12) United States Patent
Raffer

(10) Patent No.: US 6,240,770 B1
(45) Date of Patent: Jun. 5, 2001

(54) ROTARY VISCOSIMETER

(75) Inventor: Gerhard Raffer, Graz (AT)

(73) Assignee: Anton Paar GmbH, Graz (AT)

( * ) Notice: Subject to any disclaimer, the term of this patent is extended or adjusted under 35 U.S.C. 154(b) by 0 days.

(21) Appl. No.: 09/515,683

(22) Filed: Feb. 29, 2000

(30) Foreign Application Priority Data

Mar. 4, 1999 (DE) .............................................. 199 11 441

(51) Int. Cl.[7] .................................................. G02N 11/06
(52) U.S. Cl. ........................ 73/54.28; 73/54.43; 73/54.23
(58) Field of Search ............................. 73/54.28, 54.23, 73/54.31, 54.32, 54.33, 54.42, 54.43

(56) References Cited

U.S. PATENT DOCUMENTS

| | | | |
|---|---|---|---|
| 1,924,969 | * | 8/1933 | Wheeler ................................ 73/54.32 |
| 4,185,493 | * | 1/1980 | Feinstein .............................. 73/54.23 |
| 5,308,953 | * | 5/1994 | Grudzien, Jr. et al. ............... 73/54.43 |

* cited by examiner

Primary Examiner—Hezron Williams
Assistant Examiner—Michael Cygan
(74) Attorney, Agent, or Firm—Townsend and Townsend and Crew LLP

(57) ABSTRACT

A rotary viscosimeter which has a rotary measuring cylinder that is disposed in a cylindrical measuring cup holding the sample to be tested in a measuring gap formed between the cylinder and the cylindrical wall of the cup. Forces required to rotate or angularly deflect the cylinder are measured and used to determine the viscosity of the sample. The temperature of the sample in the gap is maintained uniform by constructing the measuring cup of a good heat conducting material and surrounding it with a control cup, also constructed of a good heat conducting material, and the cups are configured to form an isolation gap between them. At least one heat pump in heat conducting contact with an outer surface of the heat control cup controls the heat flow to and from the heat control cup, and a good heat conducting contact area is formed between the cups at the upper ends of the measuring cup to provide a controlled heat flow to or from the measuring cup.

20 Claims, 5 Drawing Sheets

ROTARY VISCOSIMETER

BACKGROUND OF THE INVENTION

The invention relates to rotary viscosimeters in which a test sample is placed into a cylindrical measuring cup. A rotary measuring cylinder extends into the cup so that the sample is disposed in a gap between the cylinder and the cylindrical wall of the cup. Forces required to rotate or angularly deflect the cylinder are measured and used to determine the viscosity of the sample.

FIG. 1 schematically illustrates a known rotary viscosimeter which employs a rotary cylinder and which forms the basis for the present invention. Such a rotary viscosimeter uses a measuring motor 1 which rotates a measuring cylinder 7 via a shaft 4. The relationship between the torque on the motor shaft and its electrical supply, particularly its current consumption, frequency or phase shift, are known. The torque generated by a test sample 6 can therefore be determined from a parameter of the electric supply for the motor. In addition, an angle sensor 2 is provided for determining the angular rotational position of shaft 4 or the number of its rotations. Also important is a bearing for journalling shaft 4. Depending on the constructional details and the required torques, roller bearings or, as in the illustrated case, air bearings 3 can be used.

Generally speaking, three different measuring systems with standardized geometry are in use, and they include cone/plate measuring systems, plate/plate measuring systems and, as shown in FIG. 1, cylinder measuring systems.

Such a rotary viscosimeter further has a relatively rigid support 8 for measuring motor 1 and bearings 3. The support holds a measuring cup 5 which receives sample 6, measuring cylinder 7 and, if applicable, a temperature control system for maintaining a constant sample temperature.

For determining the parameters of the sample, the torque can be measured by rotating shaft 4 at a constant rpm (CSR test). It is also possible to apply a constant torque to shaft 4 and to measure the rpm or rotational deflection of the shaft (CSS test). Finally, shaft 4 can be subjected to a sinusoidally or otherwise oscillating rotational movement (oscillation test). This last testing method permits one to determine the elastic component of sample 6 in addition to its viscosity.

Samples 6 can be liquids, gels, pastes, melts, as well as granulates or powder made from solid bodies. The viscosity of such samples is highly dependent on the temperature, which frequently can change as much as 10% per 1° C. An accurate determination of the viscosity therefor requires a homogeneous temperature distribution within the sample, particularly the portion thereof in measuring gap 10. Since the viscosity of many samples, such as heat curing cements and resins, also changes with time, it is desirable to heat or cool the sample and attain a uniform sample temperature in as short a time as possible.

FIG. 2 schematically illustrates a coaxial cylinder measuring system. Sample 6 that is to be measured is in a gap 10 between the inner surface of a stationary measuring cup 6 having a radius "R" and measuring cylinder 7 which has a radius "r", a height "h", and is driven by motor 1. The sample completely surrounds the measuring cylinder. Upon rotation of measuring cylinder 7, the sample in gap 10 is sheared and its viscosity can be determined from the rpm, the torque, and the geometry of the gap. An accurate determination of the viscosity requires a uniform temperature distribution in the sample, particularly in the area of gap 10, which has a thickness "s". In addition, the temperature of the sample must be accurately measured. Since a temperature sensor placed inside gap 10 would affect the shearing of the sample, it is necessary to measure the temperature outside the gap but as closely as possible to the sample. A convenient location for placing temperature sensor 3 is the wall of measuring cup 5.

SUMMARY OF THE INVENTION

It is an object of the invention to provide a rotary viscosimeter of the type described above which assures that the sample temperature is as uniform as possible, and which attains such a uniform temperature distribution as quickly as possible and can retain it for a relatively long period of time.

In accordance with the invention, this is attained by providing the rotary viscosimeter with a measuring cup that is surrounded by a heat control cup. An isolation gap is formed between the two cups to provide good heat isolation for the measuring cup. The measuring cup and the temperature control cup are in heat conducting contact in the vicinity of their upper circumferences to restrict heat conduction between them to that area. In addition, the temperature control cup is constructed of a material which is a good heat conductor, such as Al, a Cu alloy and the like. A fast distribution of the heat conducted to the upper portion of the measuring cup is assured by constructing it also of a material which is a good heat conductor, such as Al, a Cu alloy and the like. In this context, it is noted that undesirable heat losses or temperature increases in the measuring cup do not occur because the temperature control cup substantially prevents unwanted heat energy supply to or withdrawal from the measuring cup. A heat pump, preferably a Peltier block, controls the temperature of the temperature control cup so that heat energy is supplied to the sample in the measuring cup in a controlled manner via the upper circumferences of the cups where they are in mutual contact.

DESCRIPTION OF THE SPECIFIC EMBODIMENTS

Figure 1:
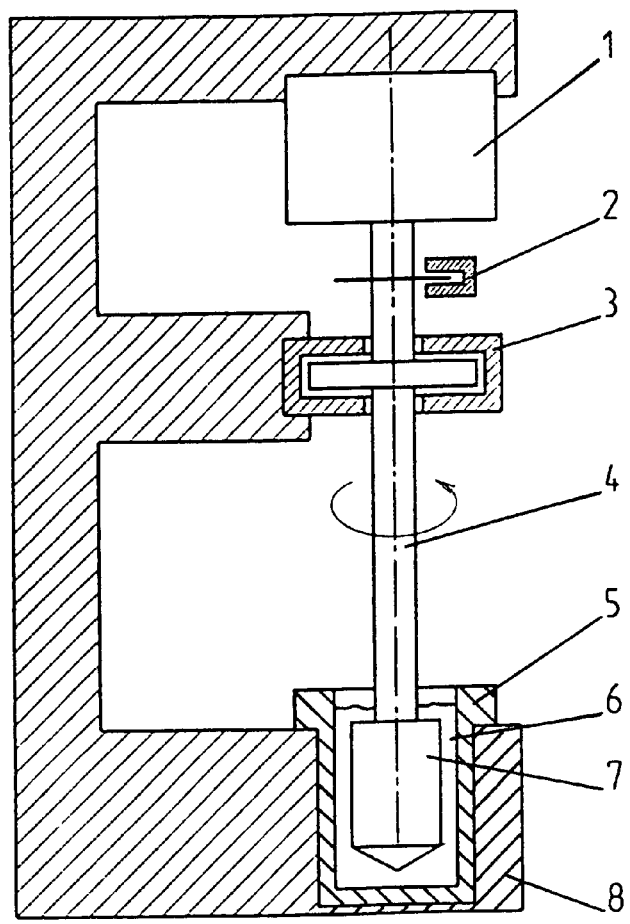
FIG. 1 schematically illustrates the principal components of a prior art rotary viscosimeter.
Figure 2:
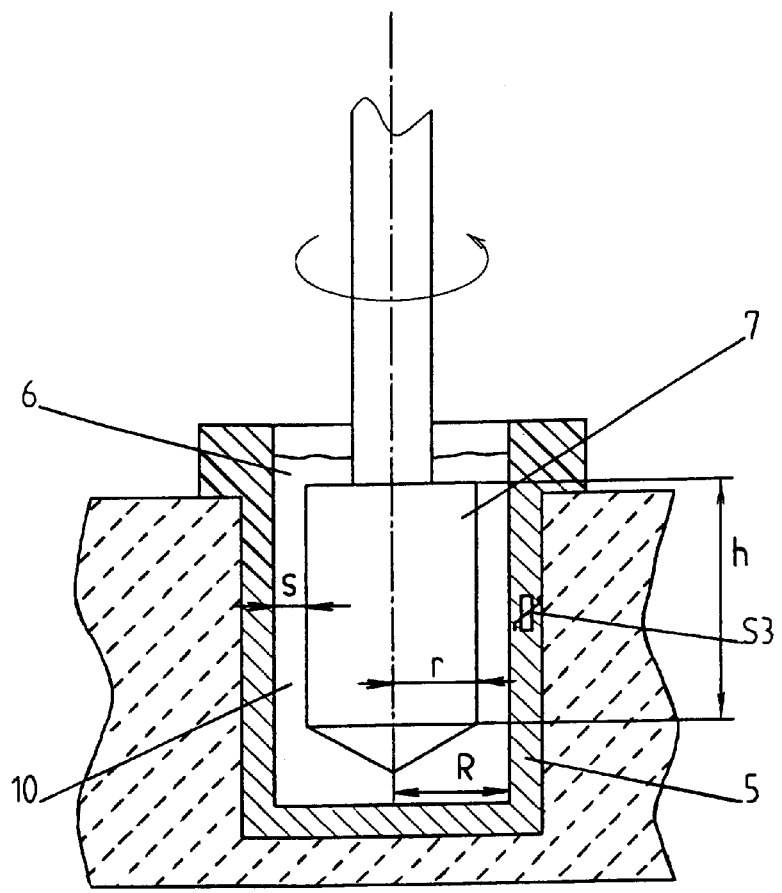
FIG. 2 is a fragmentary, side elevational view, in section, and illustrates, on an enlarged scale, a measuring cup and the rotary cylinder cooperating therewith in accordance with the prior art.
Figure 3:
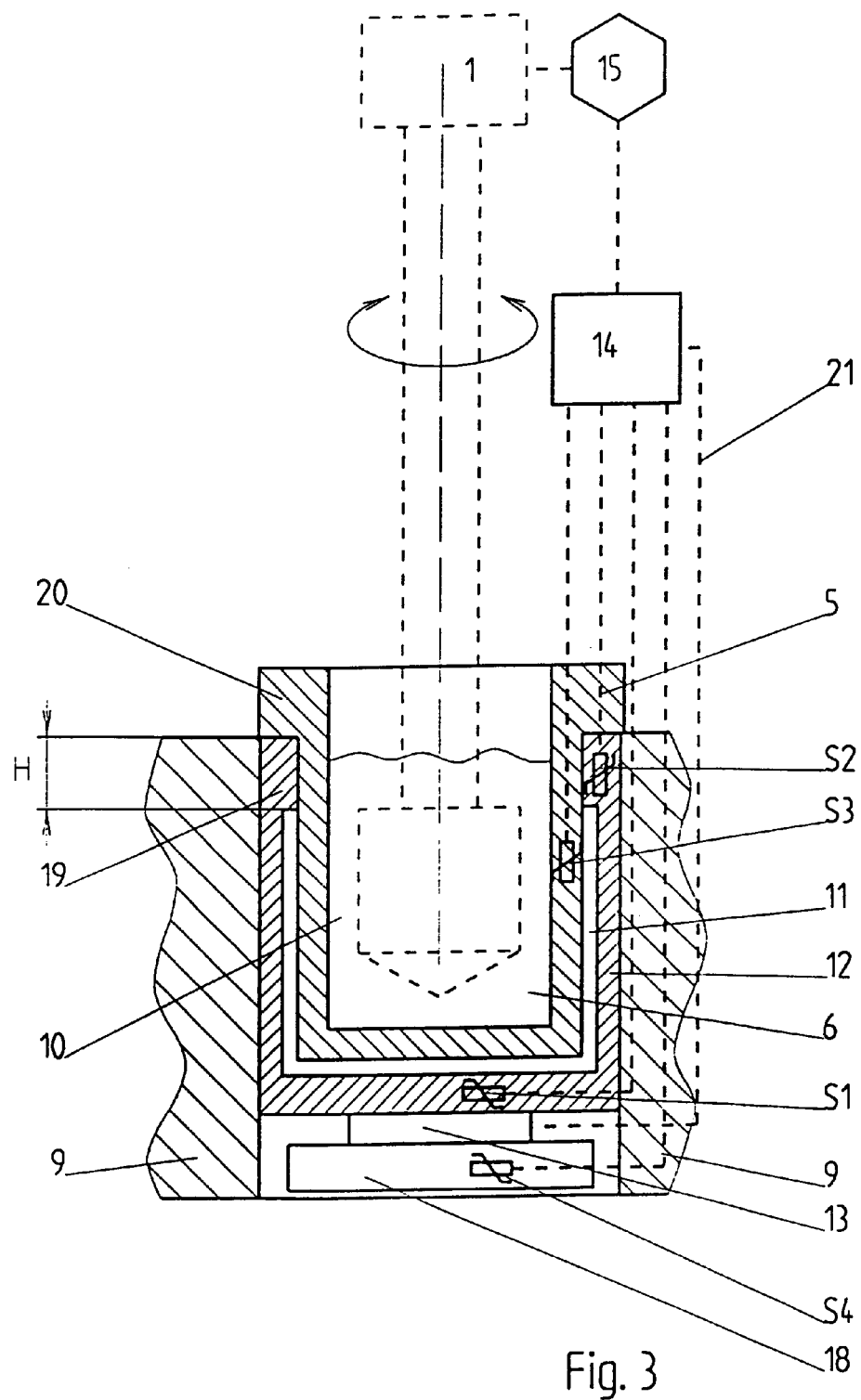
FIG. 3 is a schematic, fragmentary side elevational view, in section, of a rotary viscosimeter constructed in accordance with the invention.

Referring to FIG. 3, a measuring cup 5 is disposed inside a temperature control cup 12 (hereafter "control cup"). The cups form an isolation gap 11 between them. The upper end of the control cup 12 has a radially inwardly projecting flange 19. A radially outwardly extending flange 20 formed at the upper end of the measuring cup has a downwardly facing surface which is supported by and in good heat conducting contact with an upwardly facing surface of flange 19. The measuring cup and the control cup form a tight sliding fit, or a press-fit, to assure good heat conduction between them. In addition, a heat conducting cement or paste can be applied to the mating surfaces of the cups to further enhance the heat conduction between them in the areas where they are in mutual contact. A good heat conducting connection is also attained by forming a longitudinal slit in the upper end of control cup 12 so that the opposing wall portions of the cup separated by the slit can be drawn towards each other to establish firm contact with the wall of the measuring cup, for example by means of a tightening screw (not shown), for generating a tight circumferential fit, e.g. a press-fit, between the cups.

Figure 5:
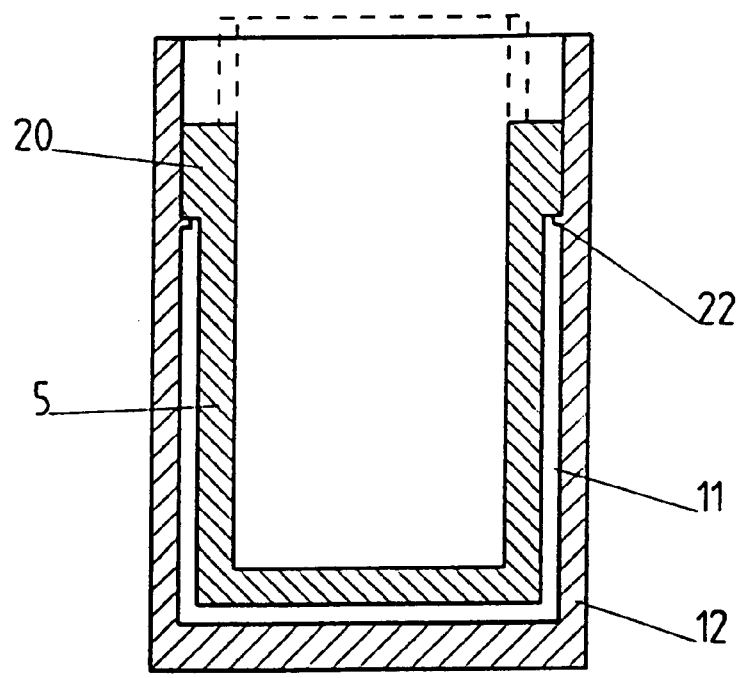
FIG. 5 is a schematic, side elevational view, in section, of another embodiment of the present invention.

Referring to FIG. 5, in another embodiment, only measuring cup 5 is provided with a circumferential, outwardly extending flange 20 which is in contact with the inner wall surface of a surrounding temperature control cup 12. The wall of measuring cup 5 can extend upwardly beyond flange 20, as is illustrated in phantom lines. A support arrangement 22 holds measuring cup 5 in the operative position. Other forms and means for establishing good heat conducting contact with the upper portion of the measuring cup can of course be employed.

It is also possible to provide control cup 12 with an inwardly extending flange 19 that is in heat conducting contact with the outer surface of measuring cup 5. If no press-fit is formed between the cups, a support arrangement 20 is provided to maintain isolation gap 11 along the base area of the cup.

Referring to FIG. 3, it is preferred to give circumferential flange 20 of measuring cup 5 and flange 19 of control cup 12 a height "H" that is between 10 and 30%, and preferably between 15 and 25% of the total height of the measuring cup. This assures that heat is rapidly conducted between the cups.

A heat pump 13, preferably a Peltier block, is positioned in the vicinity of the lower end, i.e. the base of control cup 12, for heating or cooling the control cup. A temperature regulator 14 controls the electric current supplied to heat pump 13 or Peltier block via a lead 21 to control the heating or cooling provided by the heat pump or the Peltier block. The temperature regulator 14 and measuring motor 1 are coupled to a control and evaluation unit 15 which may also include appropriate display and/or recording devices.

A principal function of the temperature control cup 12 is to conduct heat between Peltier block 13 and the upper portion of measuring cup 5 by directing heat energy to or withdrawing it from the measuring cup, as may be required for a particular test. Control cup 12 is constructed of a good heat conducting material to minimize the temperature difference between the contact surface of the Peltier block 13 and the contact surface of measuring cup 5. In addition, measuring cup 5 should be filled with sample 6 to a level that is at least as high as the mutual contact surfaces of the cups where heat is conducted between them and/or by positioning the upper end of measuring cylinder 7 at or below the height of circumferential flanges 19, 20 of cups 12 and 5, respectively. This assures maximum thermal isolation of the sample portion in measurement gap 10 from the surroundings.

An isolation gap 11 is formed between measuring cup 5 and control cup 12. The isolation gap is an air gap, or it is filled with a heat insulating material. Heat supplied by control cup 12 to measuring cup 5, which is also constructed of a good heat conducting material, flows from flange 19 of cup 12 both downwardly to the base of measuring cup 5 and upwardly to its ring flange 20. Only a very small amount of heat is conducted to or from the lower portion of measuring cup 5 because that portion of the cup is completely surrounded by control cup 12 and, therefore, there is only a very small temperature difference between them in that area. Consequently, the portion of the measuring cup which defines measuring gap 10 is in substantial thermal equilibrium, and the formation of temperature gradients in the area that is most important for the viscosity measurements is effectively prevented. The upper portion of the measuring cup 5 is in good thermal contact with the control cup so that relatively more heat energy can be supplied to or withdrawn from that portion of the cup to thereby compensate for the relatively larger temperature variations that are encountered there as a result of contact with the surroundings.

Temperature sensors are provided for measuring temperatures and controlling heat pump 13. A temperature sensor $S_1$ can be placed in the wall or the base of heat control cup 12 at a location which is directly in front of (e.g. above as seen in FIG. 3) the heat pump.

A temperature sensor $S_2$ can be placed in the upper portion of the temperature control cup, e.g. in the vicinity of ring flange 19. Sensor $S_2$, especially when it is located where measuring cup 5 and control cup 12 are in contact, like sensor $S_1$, can be used for setting the actual temperature value for control purposes. Temperature sensors $S_1$ and $S_2$ are alternatively provided.

The temperature of test sample 6 is measured with a sensor $S_3$ which is located in the wall of measuring cup 5 in the vicinity of measuring cup 10.

A temperature sensor $S_4$ is located in a heat exchanger 18 and is used for controlling the temperature of heat pump 13 to prevent a thermal overload on the Peltier block.

Signals emitted by temperature sensors $S_1$ or $S_2$, $S_3$ and $S_4$ are fed to temperature regulator 14 which, in combination with control and evaluation unit 15, which may include a microprocessor, effects the required controls and adjustments.

A precise control is attained when heat pump 13 is controlled by temperature sensor $S_1$ which is located in the wall of control cup 12 that is connected to heat pump 13. Good control is also attained when heat pump 13 is controlled by temperature sensor $S_2$, particularly when the sensor is located in the vicinity where measuring cup 5 and control cup 12 are in heat conducting contact. An especially advantageous temperature control is attained when a further temperature sensor $S_3$ is placed in the cylindrical wall of measuring cup 5 and is used for determining the actual temperature of the wall of the measuring cup. In such a case, the temperature measured by sensor $S_1$ or $S_2$ is used in an internal control circuit, and a difference signal between the temperature measured by sensor $S_1$ or $S_2$ and sensor $S_3$ is used in an outer control circuit. The outputs of the sensors are combined into a cascading control circuit for heat pump 13, and in particular for regulating the current supply to the Peltier block.

Figure 4:
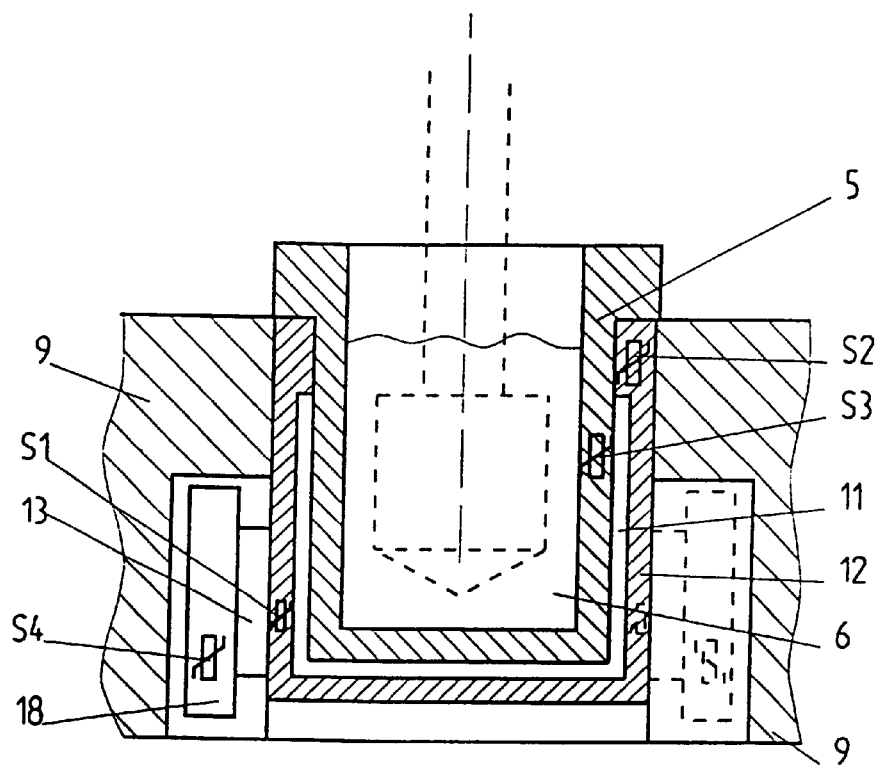
FIG. 4 is a fragmentary, side elevational view, in section, similar to FIG. 3 and illustrates further aspects of the present invention.

Referring to FIG. 4, in a further embodiment of the rotary viscosimeter, a heat pump 13 is placed in the side wall of control cup 12. FIG. 4 illustrates that more than one such heat pump can be connected to the control cup 12. If a plurality of heat pumps are used, a corresponding plurality of temperature sensors $S_4$ are provided.

For maintaining a constant temperature, it is advantageous to surround the Peltier block(s) 13 and/or the underside of control cup 12 with insulation material 9 to prevent heat losses or absorptions. Heat pump 13, and especially Peltier block 14, should be operatively coupled with a heat exchanger 18 that is in heat exchanging contact with surrounding air.

It is advantageous to attach Peltier blocks 13 in the vicinity of isolation gap 11 and to space them some distance from the upper end of the measuring and control cups 5, 12, e.g. to space them from ring flanges 19 and 20.

Except as shown, the control and construction of the rotary viscosimeter of FIG. 4 are the same as those of the rotary viscosimeter shown in FIG. 3.

A particularly advantageous embodiment of the invention uses a single Peltier element 13 and places it at the base of control cup 12.

It is advantageous to place temperature sensor $S_1$ directly in front of Peltier block 13 in the base of control cup 12, to place temperature sensor $S_3$ at the height of measuring cup 10, and to regulate the Peltier block with these two sensors.

It can alternatively be advantageous to omit temperature sensor $S_3$. In such a case, Peltier block 13 is regulated with sensor $S_1$ and sensor $S_2$ located in the upper end, a thickened transfer area, or the illustrated ring flange of control cup 12.

When completely filled, the sample level in measuring cup 5 should at least be as high as the lower end of contact between measuring cup 5 and control cup 12. A useful filling level is illustrated in FIGS. 3 and 4.

I claim:

1. A rotary viscosimeter for determining a resistance exerted by a sample disposed in a measuring gap formed by an inner surface of a measuring cup arranged about and spaced from a rotary measuring cylinder, the viscosimeter comprising a measuring cup constructed of a good heat conducting material; a heat control cup constructed of a good heat conducting material and surrounding the measuring gap, the heat control cup being spaced from the measuring cup to form an isolation gap between the cups; at least one heat pump in heat conducting contact with an outer surface of the heat control cup for controlling heat flow to and from the heat control cup; and a good heat conducting contact area between the cups and arranged in a vicinity of an upper end of the measuring cup only.

2. A viscosimeter according to claim 1 wherein the heat pump comprises a Peltier block.

3. A viscosimeter according to claim 1 wherein the contact area between the cups comprises circumferential surfaces of the cups.

4. A viscosimeter according to claim 1 wherein the contact area between the cups is formed by a sliding contact fit between surfaces of the cups.

5. A viscosimeter according to claim 1 wherein the heat conducting contact area between the cups is formed by a press-fit between surfaces of the cups.

6. A viscosimeter according to claim 1 including one of a heat conducting paste and heat conducting cement between surfaces of the cups forming the contact area.

7. A viscosimeter according to claim 1 wherein the heat control cup includes a longitudinal slit in its upper portion proximate the contact area, the slit defining opposing, spaced-apart wall portions, and including a tightening member operatively coupled with the wall portions for moving ends of the opposing wall portions towards each other to thereby establish a heat conducting press-fit between the measuring cup and the heat control cup.

8. A viscosimeter according to claim 1 wherein the heat pump is attached to a portion of the outer surface of the heat control cup which is spaced from the contact area between the cups.

9. A viscosimeter according to claim 8 wherein the portion of the outer surface of the heat control cup overlies the isolation gap between the cups.

10. A viscosimeter according to claim 1 including a first temperature sensor for controlling the heat pump, the first temperature sensor being located in one of a first portion of the control cup in close proximity to where the heat pump is in contact with the control cup and a second portion of the control cup in a vicinity of the contact area between the cups.

11. A viscosimeter according to claim 10 including a second temperature sensor for determining the actual temperature of the wall of the measuring cup in a vicinity of the measuring gap; an inner control circuit for generating first control signals which are a function of the temperature sensed by the first temperature sensor; and an outer control circuit for generating second control signals which are a function of a difference between the temperature sensed by the first temperature sensor and the second temperature sensor, the first and second control signals being combined into a cascading control for regulating the heat pump.

12. A viscosimeter according to claim 1 wherein the control cup forms a ring flange having an upwardly facing end surface at an upper end of the control cup, and wherein the measuring cup has an outwardly extending ring flange at an upper end of the measuring cup which is in abutting contact with the upwardly facing surface of the ring flange of the control cup.

13. A viscosimeter according to claim 12 wherein the control cup has an inwardly extending ring flange defining the upwardly facing end surface, and wherein the inwardly extending ring flange of the control cup has a width which corresponds to a width of the isolation gap.

14. A viscosimeter according to claim 1 including a heat exchanger operatively coupled with the heat pump and subjected to one of surrounding air and a heat exchanging fluid.

15. A viscosimeter according to claim 1 wherein the contact area between the cups extends over a height in the range of between 10% to 30% of the height of the measuring cup.

16. A viscosimeter according to claim 15 wherein the contact area extends over a height in the range between 15% to 25% of the height of the measuring cup.

17. A viscosimeter according to claim 1 including a sample disposed in the measuring cup to a level which is at least as high from a base of the measuring cup as the contact area.

18. A viscosimeter according to claim 1 wherein an upper end of the measuring cylinder is located below an upper end of the contact area between the cups.

19. A viscosimeter according to claim 1 including a heat insulating material placed over at least one of the heat control cup, a portion of a flange formed at an upper end of the measuring cup, and the heat pump.

20. A viscosimeter according to claim 1 wherein the cups are cylindrical and at least one cup forms a radially projecting wall enlargement, and wherein the enlargement defines a portion of the contact area between the cups.

* * * * *